United States Patent
Vellutato, Jr.

(10) Patent No.: US 10,571,369 B2
(45) Date of Patent: Feb. 25, 2020

(54) ERGONOMIC MICROBIAL AIR SAMPLER

(75) Inventor: Arthur L. Vellutato, Jr., Exton, PA (US)

(73) Assignee: Veltek Associates, Inc., Malvern, PA (US)

( * ) Notice: Subject to any disclaimer, the term of this patent is extended or adjusted under 35 U.S.C. 154(b) by 0 days.

(21) Appl. No.: 13/547,895

(22) Filed: Jul. 12, 2012

(65) Prior Publication Data

US 2014/0013866 A1    Jan. 16, 2014

(51) Int. Cl.
| G01N 1/22 | (2006.01) |
| B65D 43/06 | (2006.01) |
| B65D 23/10 | (2006.01) |
| B65D 8/00 | (2006.01) |

(52) U.S. Cl.
CPC ............ *G01N 1/2273* (2013.01); *G01N 1/22* (2013.01); *B65D 7/04* (2013.01); *B65D 23/102* (2013.01); *B65D 43/06* (2013.01); *G01N 2001/2276* (2013.01); *G01N 2001/2291* (2013.01)

(58) Field of Classification Search
CPC .... G01N 1/22; G01N 1/2202; G01N 1/22108; G01N 1/2273; G01N 2001/2223; G01N 2001/2276; G01N 2001/2291; C12M 23/10; B65D 43/06; B65D 2221/00; B65D 2543/00074; B65D 2543/00092; B65D 23/102; B65D 7/04; A61B 2017/00424; A61B 17/2909; A61M 5/3137; A61M 2005/3139; B25G 1/102; B26B 21/522; B43K 23/008
USPC ................... 73/864.51; 2/864.51; 435/305.4; D9/443, 530; D24/224; 16/430
See application file for complete search history.

(56) References Cited

U.S. PATENT DOCUMENTS

| | | | |
|---|---|---|---|
| D157,337 S * | 2/1950 | Britt | D24/224 |
| 2,950,833 A | 8/1960 | Short | |
| 3,055,808 A | 9/1962 | Henderson | |
| 4,908,319 A * | 3/1990 | Smyczek et al. | 435/305.4 |
| 5,421,214 A | 6/1995 | Burgdorfer | |
| 5,831,182 A | 11/1998 | Swenson | |
| 5,873,148 A * | 2/1999 | Arnold | B25G 1/043 16/422 |
| D412,810 S | 8/1999 | Alfred | |
| 6,341,014 B1 | 1/2002 | Maurel et al. | |

(Continued)

FOREIGN PATENT DOCUMENTS

WO    WO-2009100184 A1    8/2009

OTHER PUBLICATIONS

Cleanroom_Disinfectant_Veltek Catalog_Part_2.pdf, downloaded Dec. 30, 2013, http://www.pmtfrance.fr/uploads/mit_download/VAICatalog07EURO.pdf, pp. 92 and 94.*

(Continued)

*Primary Examiner* — Herbert K Roberts
(74) *Attorney, Agent, or Firm* — Blank Rome LLP

(57) ABSTRACT

A gas sampler device has a top plate with a concaved outer wall. The concaved outer wall allows users easily to lift the top plate off of the bottom plate without disturbing the bottom plate because the curved surface permits more positive contact between the outer wall and users' fingers. Moreover, the weight of the top plate is reduced by approximately twenty percent compared to conventional top plates, a feature that also makes it easier for users to lift the top plate off of the bottom plate.

14 Claims, 2 Drawing Sheets

(56) References Cited

U.S. PATENT DOCUMENTS

| | | | |
|---|---|---|---|
| 6,431,014 B1 | 8/2002 | Liu et al. | |
| 6,472,203 B1 | 10/2002 | Gallup et al. | |
| 6,565,638 B1 | 5/2003 | Sugita et al. | |
| 6,637,962 B1 * | 10/2003 | Roche | B43K 5/005 16/430 |
| 6,911,343 B2 | 6/2005 | Schembri et al. | |
| 7,208,123 B2 | 4/2007 | Knollenberg et al. | |
| 7,421,911 B2 | 9/2008 | Desrochers et al. | |
| 7,940,188 B2 | 5/2011 | Calio et al. | |
| 2001/0054621 A1 * | 12/2001 | Weber | B05B 11/3052 222/108 |
| 2004/0115096 A1 | 6/2004 | Itoh | |
| 2005/0058575 A1 | 3/2005 | Ishikawa et al. | |
| 2007/0044577 A1 | 3/2007 | Trakumas et al. | |
| 2008/0087108 A1 | 4/2008 | Kreikebaum et al. | |
| 2009/0190991 A1 * | 7/2009 | Pink | 401/6 |
| 2010/0171625 A1 | 7/2010 | Calio | |
| 2010/0212436 A1 | 8/2010 | Swenson et al. | |
| 2011/0167931 A1 | 7/2011 | Vellutato, Jr. | |

OTHER PUBLICATIONS

Thermo Scientific Single Stage N6, Andersen Cascade Impactor, Microbial, viable particle sizing sampler, Part of Thermo Fisher Scientific, Dec. 2009, Thermo Fisher Scientific Inc., 2 pgs.

Copley Scientific, Quality Solutions for Air Sampling & Particle Analysis, 2006 Edition, Copley Scientific AG, www.copleyscientific.com, pp. 1-27.

Environmental Control Monitoring Division, Veltek Associates, Inc, http://web.archive.org/web/20081010142807/http://www.sterile.com/pages/products/products-environmental-control-monitoring.htm, 2 pages, Oct. 10, 2008.

Veltek Associates, Inc. Environmental Products-SMA Atrium, http://web.archive.org/web/20081119084422/http://www.sterile.com/pages/products/environmental/sma-atrium.htm, 2 pages, Nov. 19, 2008.

Veltek Associates Inc., -SMA Atrium, http://web.archive.org/web/20061123232739/http://www.sterile.com/store/view-item-list.aspx?PlacementID=112, 7 pages, Nov. 23, 2006.

Veltek Associates Inc., Atrium 316 Stainless Steel SMA 18 ml.fill, http://web.archive.org/web/20061123233126/http://www.sterile.com/store/item-pop-up.aspx?ItemID=SMA-316-18-1/4, 1 page, Nov. 23, 2006.

International Search Report for PCT/US2013/044783, dated Jul. 15, 2013, 8 pages.

European Search Report for EP13817141.8, dated Jan. 27, 2016, 8 pages.

* cited by examiner

ERGONOMIC MICROBIAL AIR SAMPLER

BACKGROUND OF THE INVENTION

Field of the Invention

The present invention relates to a microbiological gas sampler. More particularly, the present invention is for a microbiological gas sampler for use in a controlled environment that includes an ergonomic top plate with concaved sidewalls. The concaved sidewalls allow both more positive contact when attempting to grasp the top plate and a reduction of the weight of the device.

Background of the Related Art

A controlled environment is an area which is designed, maintained, or controlled to prevent particle and microbiological contamination of products. Controlled environments include, for example, clean rooms and clean hoods. There are different levels of cleanliness in clean rooms, generally in the range of a Class 100 room (i.e., a room having no more than 100 particles of 0.5 micron and larger, per cubic foot of air), to a Class 10,000 clean room.

Clean rooms are used for a variety of purposes, such as in the manufacture of pharmaceutical products and electronics, such as semiconductors. Often, clean rooms are used to work on extremely expensive and complex products, and it is not unusual that there be millions of dollars worth of product in a clean room at any given time. Clean rooms have to maintain a high level of cleanliness, or risk large financial losses. If a product being developed or manufactured in a clean room becomes contaminated, the entire product in the clean room must often be discarded.

Microbial air samplers are used to monitor the level of cleanliness (in terms of viable contamination) in a controlled environment. One or more samplers are positioned about the clean room to collect airborne particulates and organisms (or microorganisms) such as bacteria and fungi. Samplers that run at high flow rates permit air to enter the sampler at such high flow rates that loss of smaller particulates carrying microorganisms is normality (i.e., smaller particulates are not retained in the medium). At the same time high flow rate air samplers only sample for a short time period and relay on a short snapshot of the condition of the area. Samplers running at 28.3 LPM (liters per minute) must operate for a longer period of time than a unit running at 322 LPM. In doing this, they sample a broader spectrum of the drug fill time and present superior data as the sample time takes a larger snapshot of the operation. Samplers that run at 28.3 LPM also provide the ability to capture more smaller particulates that may be lost due to dynamic drag (or an umbrella affect) in higher flow rate units.

Air sampling systems are generally known, and an air sampling system is offered by Veltek Associates, Inc. known as SMA (Sterilizable Microbiological Atrium) Microbial Air Sampler System. One such system is shown in U.S. Pub. No. 2011/0167931, filed Jan. 12, 2010, and U.S. Pat. No. 7,940,188, filed Jul. 26, 2010, the entire contents of which are hereby incorporated by reference. As noted in those applications, the air sampler system includes a controller connected to a vacuum pump to control the flow of air to air sampler devices located in the clean room.

A prior art air sampler device 5 is shown in FIGS. 1(a), (b), which is offered by Veltek Associates, Inc. The assembled air sampler device 5 includes a top plate 10 with holes 11 and a bottom plate 14. The top plate 10 has a flat section and an outer side. The flat section forms the top surface of the top plate 10 and extends substantially horizontally when in use. The openings pass through the flat section. The outer side extends downward to be substantially orthogonal to the flat section. The outer side has a single uniform thickness that extends the entire circumference of the top plate 10. The outer surfaces of the top plate 10 and the bottom plate 14 are flat and smooth. The bottom plate 14 is sized and shaped substantially the same as the top plate 10. Though the device 5 is shown as circular, other shapes may be used.

In operation, the top plate 10 is removed, a Petri dish is placed on the bottom plate 14, and the top plate 10 is replaced on the bottom plate 14. A vacuum tube is attached to the air port 22. Air is then sucked in through the holes 11 in the top plate 10, so that the air strikes a test medium contained in a Petri dish, which is inside the air sampler device 5 between the top plate 10 and the bottom plate 14. The air exits through the air port 22 and vacuum tube. At the end of the testing period, the top plate 10 is again taken off of the bottom plate 14, the Petri dish is removed, and the top plate 10 is replaced. The Petri dish can then be analyzed to determine the level of cleanliness of the clean room.

The entire device 5 is metal so that the device 5 can be sterilized by heat, steam, Vaporized Hydrogen Peroxide (VHP) or Ethylene Oxide (ETO). The Petri dish has a diameter of about 3.5 inches. The top plate 10 has an outer diameter of 4.5 inches. There are twelve holes 11 positioned within about a circular area having a 3 inch diameter, and each hole 11 has a diameter of about 0.5 inches.

However, the sides of the top plate 10 are smooth and the top plate 10 is relatively heavy, specifically, 1 pound, 4.2 ounces. Consequently, the top plate 10 can be difficult to grasp by a person inside the clean room who is wearing gloves.

SUMMARY OF THE INVENTION

Accordingly, it is an object of the invention to provide a device for sampling viable cells in air. It is another object of the invention to provide a microbial air sampler having an improved design that both decreases the weight of the top plate and allows for more positive contact when grasping the top plate.

Accordingly, an air sampler device is provided having a concaved sidewall along the outer circumference of the top plate. The concaved sidewall is particularly useful because users are often required to wear gloves at all times while inside the clean room. The concaved sidewall allows the top plate to be easily lifted off of the bottom plate without disturbing the bottom plate because more positive contact can be made between the fingers of the user and the sidewall of the top plate.

Moreover, the concaved sidewall decreases the weight of the device by approximately twenty percent. The decreased weight of the top plate also makes it easier for users to lift the top plate off of the bottom plate.

These and other objects of the invention, as well as many of the intended advantages thereof, will become more readily apparent when reference is made to the following description, taken in conjunction with the accompanying drawings.

DETAILED DESCRIPTION OF THE PREFERRED EMBODIMENTS

Figure 1A:
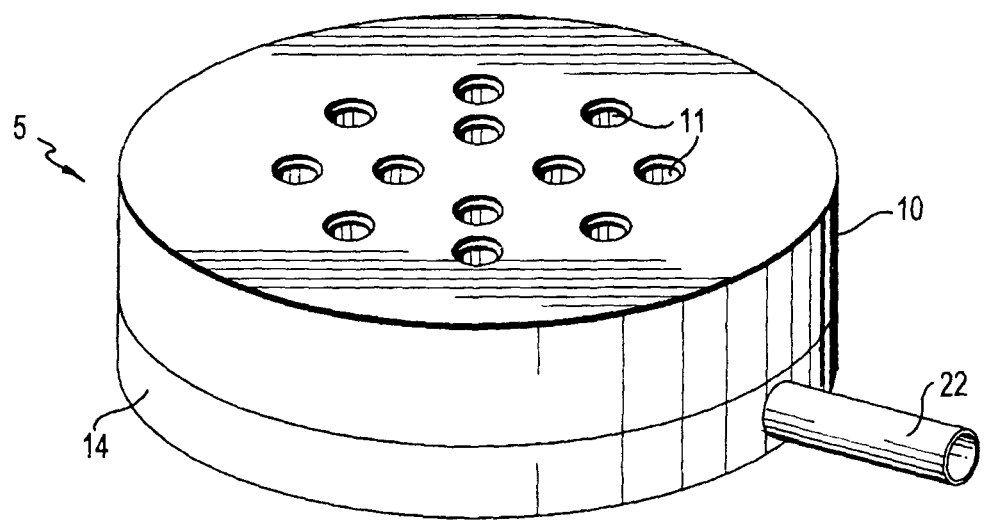
FIG. 1(a) is a perspective view of the air sampler device in accordance with the prior art.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. Preferred embodiments of the invention are described for illustrative purposes, it being understood that the invention may be embodied in other forms not specifically shown in the drawings.

Figure 2:
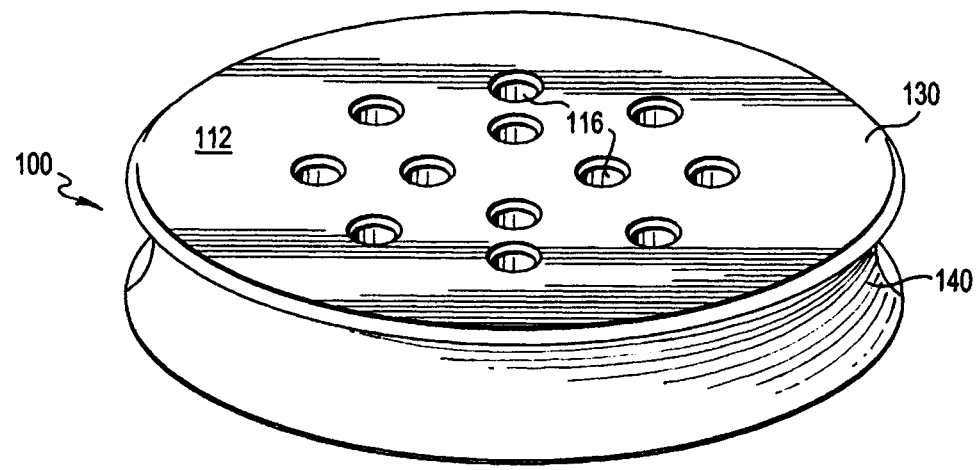
FIG. 2 is a top perspective view of the top plate of the air sampler device in accordance with an exemplary embodiment of the invention.

As shown in FIG. 2, a top plate 100 of an air sampler device 50 is shown. The top plate 100 has a top surface 112. There are twelve holes 116 formed in the top surface 112. The top plate 100 has a flat section 130 and at least one outer side 140. The flat section 130 forms the top surface of the top plate 100 and extends substantially horizontally when in use. The openings 116 pass through the flat section 130. The outer side or side wall 140 extends downward to be substantially orthogonal to the flat section 130. The side wall 140 is concaved or curved inward and defines the entire outer circumference of the top plate 100. The concaved outer side 140 makes the top plate 100 easy to grip, so that a user can easily remove and replace the top plate 100 with respect to the bottom plate 150.

Figure 3:
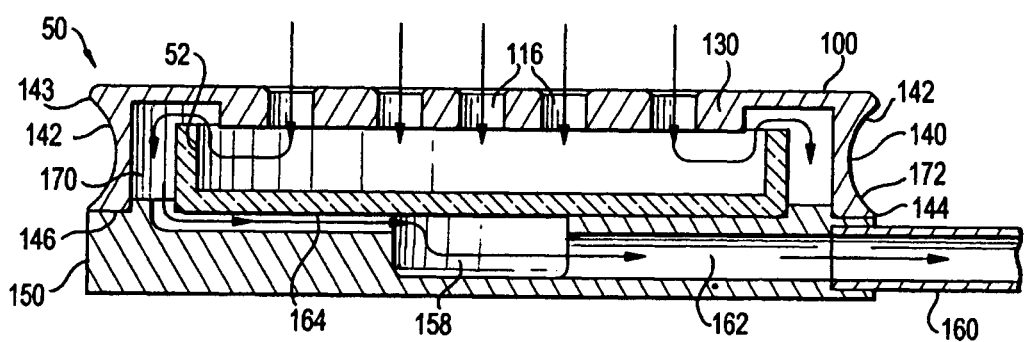
FIG. 3 is a cross-section side view of the air sampler device of FIG. 2 showing movement of air within the device.

For illustrative purposes, the bottom plate 150 is also shown in FIG. 3. A vacuum air port 160 is positioned at the side of the bottom plate and communicates with an air hole 162. The air hole 162 extends through the bottom plate 150, from the air port 160 to the center well 158. The vacuum air port 160 connects to a vacuum tube to draw air through the sampler 50.

The operation of the sampler 50 is best shown in FIG. 3, where the arrows generally show the direction of travel of the air as it flows through the device 50. A sterilized air sampler device 50 is introduced into the clean room, and the top plate 100 is removed. The Petri dish 52 is inserted onto the bottom plate 150, and the top plate 100 is replaced. The air flow is then initiated for a predetermined period of time. Air is drawn into the sampler device 50 by the vacuum tube 162 through the air port 160.

Once the air enters the holes 112 in the top plate, it strikes the capture material in the Petri dish 52, then travels up around the sides of the Petri dish 52, through the elongated slots 164 beneath the Petri dish 52, and enters the center well 158. The air is then sucked through the air hole 162 and exits out of the vacuum air port 160. Once the predetermined period of time (which can be from 10-60 minutes or longer) has lapsed, the air flow is turned off. The top plate 100 is then raised, and the Petri dish 52 is removed for testing. The sampler 50 can then be sterilized, if desired, and a new Petri dish 52 introduced.

Accordingly, the air port 160 is in flow communication with the passageway 162, which is in flow communication with the well 158. And, the well 158 is in flow communication with the elongated slots 164, which are in flow communication with air entering the holes 112 in the top plate 100. The structure and operation of the device having the bottom plate 150 shown, is more fully described in Pub. No. 2011/0167931, which is incorporated herein by reference. It should be noted, however, that any suitable bottom plate 150 can be provided other than the one shown, and the bottom plate 150 need not have a center well 158 and air hole 162 and slots 164.

As shown in FIG. 3, the side wall 140 defines a side wall inner surface 170 and a side wall outer surface 172. The inner surface 170 defines an inner diameter of the upper plate 140. The inner surface 170 is straight, and does not project inward, so as not to interfere with the Petri dish 52. Thus, the inner wall 170 need not be positioned further away from the Petri dish 52. The straight inner wall 170 also provides a straight air conduit with uniform dimensions (i.e., width) between the Petri dish 52 and the inner wall 170, so that air can flow uniformly around the Petri dish 52 to the exit port 160.

The outer surface 172 of the side wall 140 is curved, and therefore the side wall 140 has a varying thickness. The side wall 140 is thicker at the top and bottom portions, and thinner in the middle portion where it is curved inward. The outer surface 172 is curved to be ergonomic and mate with the shape of a user's gloved hand. The top of the curved outer surface 172 has a curved top lip 142 that extends around the entire circumference of the top plate 100. The top lip 142 projects outward from the middle portion of the wall 140. The top lip 142 engages the user's fingers when the top plate 100 is being lifted, thereby making it easier to lift and manipulate the top plate 100. The top lip 142 is rounded or beveled at the end 143 between the top surface of the flat section 130 and the side wall 140. The rounded end 143 enhances the safety of the top plate 100 and increases the comfort of the user, by removing any sharp angles. An additional benefit of the curved outer wall surface 172 is that the user knows by touch that he is manipulating the top plate 100 (and not the bottom plate 150). Thus, for instance, the user can slide his/her fingers up from the bottom of the device 50 until the fingers engage the top lip 142.

The bottom section of the curved outer wall surface 172 forms a bottom lip 144 that is relatively sharp. This provides the side wall 140 with a flat foot 146 that forms a seal and mates with the top surface of the bottom plate 150. The outer circumference of the foot 146 of the side wall 140 where the top plate 100 meets the bottom plate 150 is sized and configured substantially the same as the bottom plate 150. The foot of the side wall 140 of the top plate 100 has an outer diameter of 4.5 inches. There are twelve holes 116 positioned within about a circular area having a 3 inch diameter, and each hole 116 has a diameter of about 0.5 inches. The thickness of the top and bottom of the concaved side 140 is about 0.25 inches.

The concaved outer side 140 of the top plate 100 is particularly useful since users are often required to wear gloves (in addition to garments, hoods, and booties) at all times while inside the clean room. In addition, the entire device 50 is made of metal, so that it can be sterilized by heat, steam, VHP or ETO. Consequently, the top plate 100 (as well as the bottom plate) is relatively heavy, which makes it difficult to remove with a gloved hand. By providing an inwardly concaved outer side 140, the present invention allows the top plate 100 to be easily lifted off of the bottom plate 150 without disturbing the bottom plate 150.

Figure 1B:
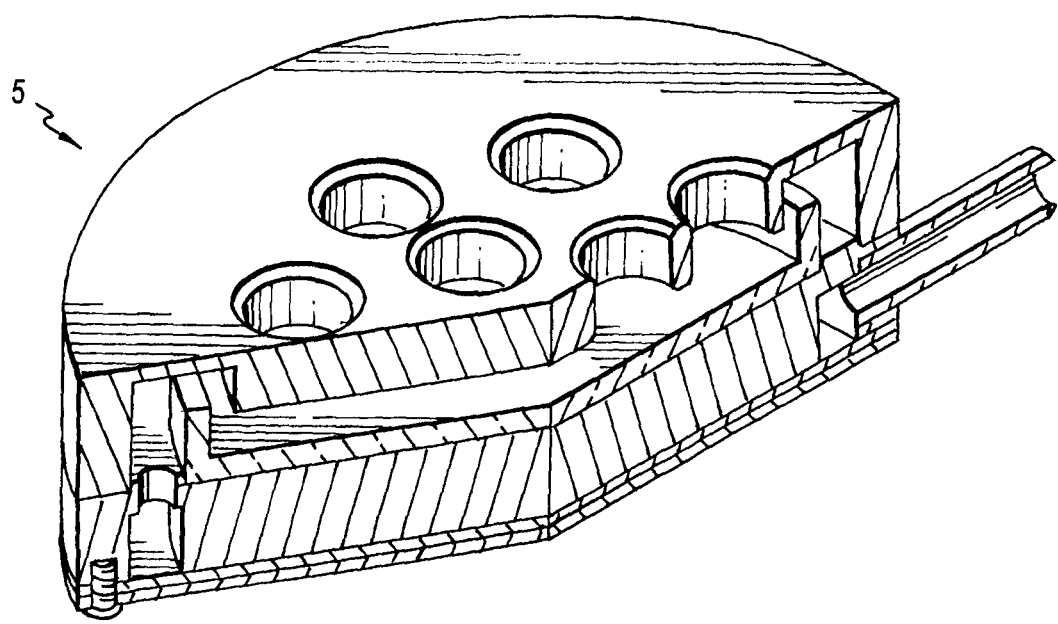
FIG. 1(b) is a cross section view of the air sampler device in accordance with the prior art.

The curved side wall 140 also substantially reduces the weight of the top plate 100. The weight of the top plate 100 is 1 pound, 1 ounce, which is about a 20% (18.82%) reduction in weight from the top plate 10 of FIG. 1, which weighs 1 pound, 4.2 ounces. The radius of curvature is about 0.337 inches.

The curved outer surface 172 is preferably uniformly curved completely around the top plate 100. However, the outer surface 172 need not be completely curved and only portions of the outer surface 172 can be curved. For instance, the side wall 140 can be curved at two opposite portions of the top plate 140. Or, the side wall 140 can be curved differently at different portions of the side wall 140. And, the curve need not have both a top lip 142 and a bottom lip 144. For instance, only a top lip 142 can be provided.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A gas sampler device comprising:
   a top plate having a top surface, a top section, and a downward turned side wall with an inner surface and an outer surface, wherein the top plate has a plurality of through holes through the top surface, the inner surface is straight and orthogonal to the top section, and an entirety of the outer surface is concaved inward, wherein the top plate has a rounded lip between the side wall and the top section, and wherein the side wall has a sharp lip opposite the rounded lip, wherein each of the rounded and sharps lips extend outwardly beyond the outer surface and wherein the outer surface terminates at the rounded and sharp lips, respectively, and a diameter of the rounded lip and a diameter of the sharp lip is the same; and
   a bottom plate having a top surface, a bottom surface, a side surface, and a receiving portion at the top surface for receiving a dish, the top surface of said bottom plate mating with the side wall of said top plate, wherein the bottom plate comprises a channel terminating at a hole in the side surface, said channel fluidically connecting the plurality of through holes of the top plate with the hole in the side surface of the bottom plate,
   wherein the top plate is separable and lifts from the bottom plate by a user's fingers gripping the rounded lip of the top plate.

2. The gas sampler device of claim 1, wherein the top plate is metal.

3. The gas sampler device of claim 1, wherein the top plate is non-compressible.

4. The gas sampler device of claim 1, wherein the side wall of said top plate is an unthreaded shaft.

5. The gas sampler device of claim 1, wherein the top plate has a weight greater than 1 pound.

6. The gas sampler device of claim 1, wherein the top plate has an outer diameter of 4.5 inches.

7. The gas sampler device of claim 1, wherein the outer surface of the downward turned side of the top plate is concaved inward with a radius of curvature of 0.337 inches.

8. The gas sampler device of claim 1, wherein a ratio of an outer diameter of the top plate to a radius of curvature of the outer surface of the downward turned side of the top plate is 13-14 to 1.

9. The gas sampler device of claim 1, wherein the rounded lip of the top plate is curved and projects outwardly from the side wall.

10. The gas sampler device of claim 1, wherein the top plate has a width and the side wall has a height such that a length of the width of the top plate is substantially greater than a length of the height of the side wall, thereby defining a wide grip.

11. A gas sampler device for use in a controlled environment, comprising:
    a top plate configured for use in the controlled environment, the top plate having a top surface, a top section, and a downward turned side wall with an inner surface and an outer surface, wherein the top plate has a plurality of through holes through the top surface, the inner surface is straight and orthogonal to the top section, and an entirety of the outer surface is concaved inward, wherein the top plate has a rounded lip between the side wall and the top section, and wherein the side wall has a sharp lip opposite the rounded lip, wherein each of the rounded and sharps lips extend outwardly beyond the outer surface and wherein the outer surface terminates at the rounded and sharp lips respectively, and a diameter of the rounded lip and a diameter of the sharp lip is the same; and
    a bottom plate having a top surface, a bottom surface, a side surface, and a receiving portion at the top surface for receiving a dish, the top surface of said bottom plate mating with the side wall of said top plate, wherein the bottom plate comprises a channel terminating at a hole in the side surface, said channel fluidically connecting the plurality of through holes of the top plate with the hole in the side surface of the bottom plate,
    wherein a thickness of the side wall at the rounded and sharp lips is greater than a thickness of a middle portion of the side wall between the rounded and sharp lips, and
    wherein the top plate is separable and lifts from the bottom plate by a user's fingers gripping the rounded lip of the top plate.

12. The gas sampler device of claim 11, wherein the controlled environment s a clean room.

13. A method for providing a gas sampler device in a controlled environment, comprising the steps of:
    providing a top plate configured for use in the controlled environment, the top plate having a top surface, a top section, and a downward turned side wall with an inner surface and an outer surface, wherein the top plate has a plurality of through holes through the top surface, the inner surface is straight and orthogonal to the top section and an entirety of the outer surface is concaved inward, wherein the top plate has a rounded lip between the side wall and the top section, wherein the side wall has a sharp lip opposite the rounded lip, and a diameter of the rounded lip and a diameter of the sharp lip is the same, and wherein each of the rounded and sharps lips extend outwardly beyond the outer surface and wherein the outer surface terminates at the rounded and sharp lips, respectively;
    providing a bottom plate having a top surface, a bottom surface, a side surface, and a receiving portion at the top surface for receiving a dish, the top surface of said bottom plate mating with the side wall of said top plate, wherein the bottom plate comprises a channel terminating at a hole in the side surface, said channel fluidically connecting the plurality of through holes of the top plate with the hole in the side surface of the bottom plate; and
    lifting the top plate from the bottom plate by a user's fingers gripping the rounded lip of the top plate.

14. The method of claim 13, wherein the gas sampler device is configured for use by a user wearing a glove and/or hood.

* * * * *